United States Patent [19]

Kurtz et al.

[11] 4,105,031
[45] Aug. 8, 1978

[54] ATTACHABLE EXPANSION CHAMBER FOR PLEURAL DRAINAGE DEVICE

[75] Inventors: Leonard D. Kurtz, Woodmere; Robert E. Bidwell, Melville, both of N.Y.

[73] Assignee: Deknatel, Inc., Long Island, N.Y.

[21] Appl. No.: 621,591

[22] Filed: Oct. 10, 1975

[51] Int. Cl.² ............................................ A61M 1/00
[52] U.S. Cl. ................................................. 128/276
[58] Field of Search .............. 128/275, 276, 277, 278, 128/2 F, 294, 295

[56] References Cited

U.S. PATENT DOCUMENTS

| | | | |
|---|---|---|---|
| 2,180,042 | 11/1939 | Ettinger | 128/276 |
| 3,363,626 | 1/1968 | Bidwell et al. | 128/276 |
| 3,620,408 | 11/1971 | Holbrook | 128/276 X |
| 3,757,783 | 9/1973 | Alley | 128/277 |
| 3,783,870 | 1/1974 | Schachet | 128/276 |
| 3,847,152 | 11/1974 | Schachet | 128/276 |
| 3,848,628 | 11/1974 | Deaton et al. | 128/276 X |
| 3,861,390 | 1/1975 | Schachet | 128/276 |
| 3,943,929 | 3/1976 | Patel | 128/275 |

FOREIGN PATENT DOCUMENTS 119,311    2/1956    U.S.S.R. .................................. 128/276

Primary Examiner—J. Reed Fisher
Attorney, Agent, or Firm—Larson, Taylor and Hinds

[57] ABSTRACT

The present invention provides an expansion chamber that can be attached to a conventional underwater drainage device used for draining a body cavity. The attaching means permits the expansion chamber to be quickly attached to the drainage device and when attached to become rigidly and securely connected thereto. The connecting means comprises fitting engageable male and female rails, one of which is connected along its side and extends from the expansion chamber and the other of which is connected along its side and extends from the drainage device. A connecting chamber is rigidly attached at one end thereof to the top of the expansion chamber and extends longitudinally therefrom. Depending from the other end and securely mounted thereto is a hollow needle. The needle can engage and penetrate a self-sealing grommet located in the top of the drainage device. In this manner, the drainage device can be used to maintain the same vacuum within the expansion chamber as within the drainage device. An outlet at the top of the expansion chamber permits connection with a thoracotomy tube to a body cavity at a location that is different from the location where the drainage device is connected.

26 Claims, 8 Drawing Figures

ATTACHABLE EXPANSION CHAMBER FOR PLEURAL DRAINAGE DEVICE

BACKGROUND OF THE INVENTION

1. Field of the Invention

This invention relates to surgical drainage systems and more particularly relates to an additional drainage apparatus attachable to the type of drainage apparatus disclosed in U.S. Pat. Nos. 3,363,626 and 3,363,627 for draining fluid from a body cavity whereby the additional drainage apparatus can be connected to the body cavity at a second location.

2. Background Of the Invention

In the aforementioned U.S. Pat. Nos. 3,363,626 and 3,363,627 to Bidwell et al, both issued Jan. 16, 1968, a brief explanation of the lung structure and of the human breathing function is described. These patents further describe and claim a drainage system and apparatus and the operation thereof for draining the pleural cavity. For purposes of brevity, reference may be made to those previous patent for such basic explanations.

Numerous other devices have been developed to maintain a vacuum in and to drain the pleural and thoracic cavities. In addition, numerous improvements have been made to the devices disclosed and claimed in the aforementioned patents. These further devices and improvements are disclosed in U.S. Pat. Nos. 3,559,647; 3,783,870; 3,847,152; 3,853,128; and 3,809,085. The devices disclosed in the aforementioned patents are generally classified as three bottle system since they provide one bottle for collecting fluids drained from the body cavity, one bottle for maintaining a water seal on the first bottle, and a third bottle connected to a vacuum pump for regulating the amount of vacuum in the first bottle.

In addition to the foregoing devices, there are also so-called four bottle systems disclosed in U.S. Pat. Nos. 3,847,152; 3,861,390; 3,783,870; and 3,757,783. The fourth bottle of the so-called four bottle system is disclosed as being added to the three bottle system for further regulating the vacuum in the first bottle.

All of the foregoing patents disclose drainage devices having only a single collection chamber or trap chamber that is connectable to the body cavity. Quite frequently it is desirable to connect more than one thoracotomy tubes to the body cavity to be drained. The use of more than one thoracotomy tube could permit one tube to be connected to a low point in the body cavity where liquids would collect and the other tube to be connected to a high point in the cavity where gases would collect. In the past, however, it was necessary to use two entire pleural drainage devices which results in added expense, additional space required to store the extra device, an additional vacuum source or numerous "Y" connections to permit one vacuum source to be used, and possible circulating fluid flows between the two drainage devices as a result of different vacuums being maintained in each device. On the other hand, if only one drainage device were used and the high and low thoractotomy tubes were connected together through a "Y" tube connection, it would be impossible to tell the flow from each thoracotomy tube.

During normal hospital procedures, the supervising physician normally directs that a first thoracotomy tube be inserted into a low point in the cavity to be drained and the tube connected to a drainage device such as that disclosed in the aforementioned patents. The supervisoring physician frequently decides to add a second thoracotomy tube to be connected to a second point in the cavity being drained. If the supervising physician desired to know the flow from the second thoracotomy tube, he will normally direct that a completely new drainage device be set up and connected to the second thoracotomy tube. Obviously, such an operation requires a significant amount of time and frequently numerous personnel to effect the connection in a rapid manner. Thereafter, it has occasionally been decided that still further drainage points are desired from the body cavity or that a second body cavity has to be drained and the same vacuum has to be applied to both body cavities. It can easily be seen that the more thoracotomy tubes that are used, the greater the complexity in maintaining the same vacuums, in setting up and supervising each of the scattered devices, and additional times required to set up the added devices.

Thus, there is the need for an expandable drainage system that uses the same vacuum source, but yet will still provide separate collection chambers for each thoracotomy tube so that the flow through each tube can be separately observed. Finally, there is the need for expansion chambers that are rigidly attachable to the principal drainage device so that all of the collection chambers can be retained in the same location.

SUMMARY OF THE INVENTION

The present invention provides for a surgical drainage system that overcomes the disadvantages associated with the prior art devices noted hereinabove. The present invention permits a separate expansion chamber to be added to a single principal drainage device for each separate thoracotomy tube and point in the body cavity to be drained. An inexpensive expansion chamber is disclosed and claimed which can be quickly and easily physically mounted to the principal drainage device and placed in fluid communication therewith so that the same vacuum can be maintained in the added expansion chamber as that being maintained in the collection chamber of the principal device. In addition, the present invention is of simple construction, inexpensive, easily stored, and easily maintained in a sterilized state.

In accordance with the invention, an expansion chamber is provided which is mountable on a drainage device that is used for draining fluids from a body cavity. The drainage device has a collection chamber and a means for placing the collection chamber in fluid communication with the cavity to be drained. The expansion chamber provides an additional collection chamber and comprises an inlet opening adapted to be placed in fluid communication with the cavity to be drained. The expansion chamber further comprises means for rigidly mounting the expansion chamber on the drainage device and a means for substantially equalizing the absolute pressure in the expansion chamber with the absolute pressure in the collection chamber of the drainage device. The present invention can also be viewed as an improvement to a drainage system for draining a pleural cavity wherein the drainage system includes a drainage device for draining extraneous fluids from the cavity and for applying a vacuum to the cavity. The drainage device comprises a collection chamber and an underwater seal chamber. The collection chamber has located at its upper end an outlet opening and an inlet opening adapted to be placed in fluid communication with the cavity to be drained. The seal chamber also has located at its upper end an inlet opening and an outlet opening, the inlet opening being in fluid communication with the collection chamber outlet and exposed to pressure conditions in the collection chamber. The seal chamber outlet opening is exposed to pressure conditions other than the pressure conditions in the collection chamber. In addition to the aforesaid device, devive, the drainage system further comprises an expansion chamber mounted on the drainage device for also draining fluids from the same body cavity and a means for rigidly mounting the expansion chamber on the drainage device. In addition, the expansion chamber has an inlet opening adapted to be placed in fluid communication with the body cavity, an outlet opening in the expansion chamber, and means for exposing the expansion chamber outlet to pressure conditions in the collection chamber.

In one embodiment of the preferred invention, there is a hollow connecting chamber rigidly mounted at one end to the expansion chamber and extending therefrom. A hollow needle is mounted on and depends from the other end of the connecting chamber and is insertable into a self-sealing grommet or diaphragm in an opening located at the top of the collecting chamber of the drainage device.

In a further embodiment of the invention, a mounting means for mounting the expansion chamber to the principal drainage device is disclosed whereby the mounting means comprises a pair of elongated rails respectively mounted along one side thereof to and extending substantially coplanar with the expansion chamber and the drainage device. One of the rails comprises in cross section a substantially U-shaped female rail and the other rail comprises in cross section a male rail for coaxially mating with and being engaged along the outer edges thereof by the female rail. The disclosed mounting means provides an easily and quickly attachable means for mounting the expansion chamber onto the drainage device. Both the drainage device and the expansion chamber can be inexpensively manufactured with one of the rails integral therewith. When attached, the mounting means substantially locks together the expansion chamber and the drainage device in a rigid manner such that the entire system can be safely handled by either one without the two becoming uncoupled.

These and other features and advantages of the present invention will be set forth in, or apparent from, the detailed description of the presently preferred embodiment of the invention found hereinbelow.

DETAILED DESCRIPTION OF THE PREFERRED EMBODIMENT

Figure 1:
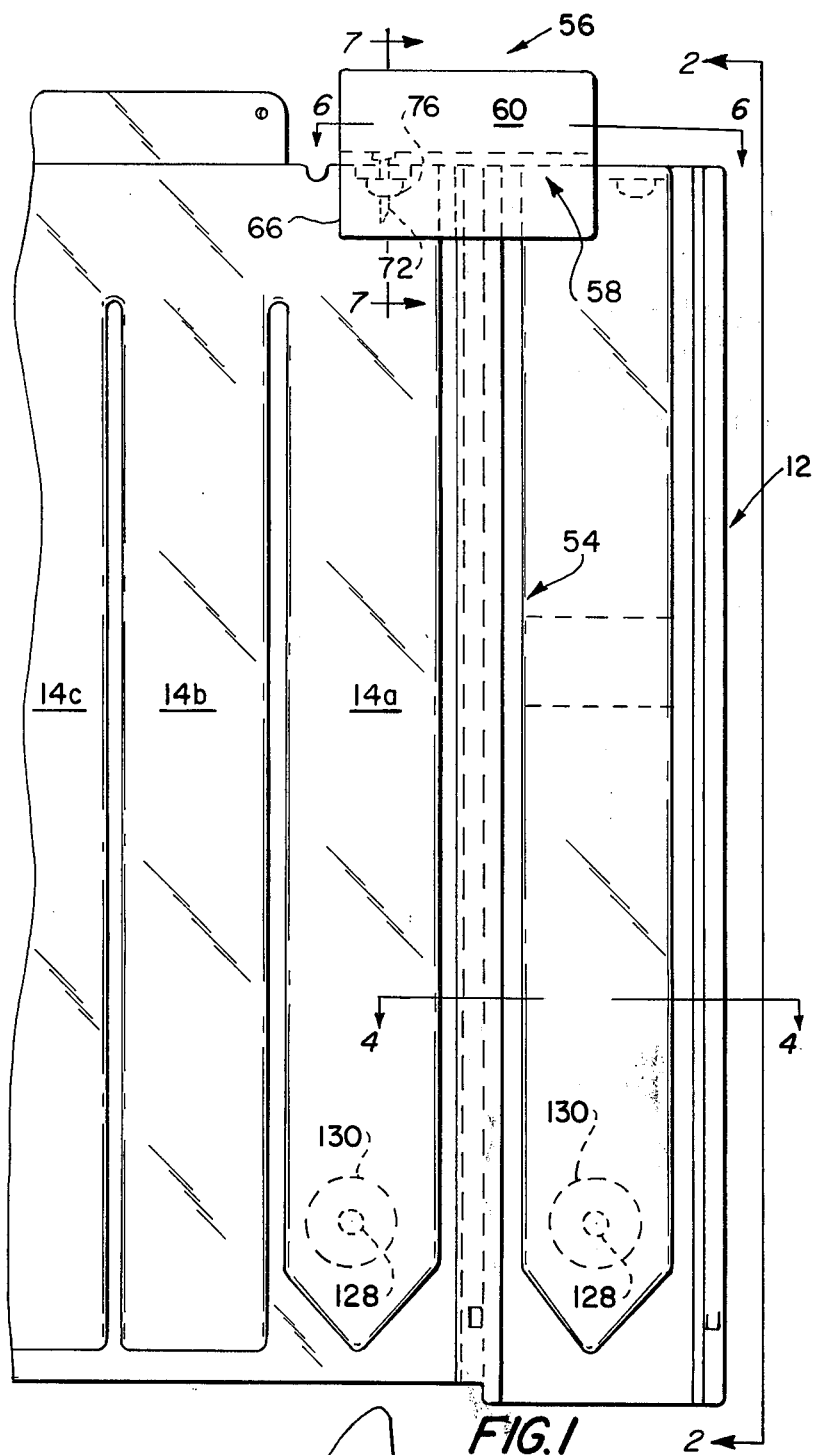
FIG. 1 is a front elevational view of a drainage system according to the present invention showing the expansion chamber connected to a drainage device, only part of the drainage device being shown.

With reference now to the figures wherein like numerals depict like elements throughout the several views, a drainage system for draining a body cavity is depicted. With specific reference to FIG. 3, the drainage system comprises an underwater drainage device 10 rigidly coupled to two expansion chambers 12. Although underwater drainage device 10 is described in detail in the aforementioned Bidwell et al U.S. Pat. Nos. 3,363,626 and 3,363,627, which are incorporated by reference herein and are expressly made a part hereof, the parts of underwater drainage device 10 will be described in further detail so that the overall operation of the drainage system can be appreciated. Drainage device 10 comprises a collection chamber 14 divided into three separate subchambers 14a, 14b and 14c which are in fluid communication with each other at the tops thereof. An inlet opening 16 is located at the top of subchamber 14a of collection chamber 14. A thoracotomy tube is shown at 18 and is connected in a sealing relationship to inlet opening 16 at one end and is connectable to the body cavity to be drained at the other end. Thus, thoracotomy tube 18 places inlet opening 16 in fluid communication with the body cavity to be drained. Collection chamber 14 also includes an outlet opening 20 located at the top or upper end thereof.

Underwater drainage device 10 further comprises a U-shaped seal chamber 22 having located at the upper end thereof an inlet opening 24 and an outlet opening 26. Seal chamber inlet opening 24 is in fluid communication with collection chamber outlet opening 20 and is exposed to pressure conditions in collection chamber 14. Seal chamber outlet opening 26 is exposed to pressure conditions other than the pressure conditions in collection chamber 14, namely the pressure developed by a vacuum pump 28.

Finally, underwater drainage device 10 comprises a U-shaped manometer 30 for regulating the vacuum in drainage device 10. Manometer 30 has an outlet opening 32 located at the top of one arm of the U-shaped manometer and an inlet opening 34 at the top of the other arm. Manometer inlet opening 34 is in communication with seal chamber outlet opening 26. Manometer outlet opening 32 is open to atmospheric pressure and a water seal located in manometer 30 is used to regulate the vacuum maintained in drainage device 10 (discussed in detail in the aforementioned patents).

Figure 2:
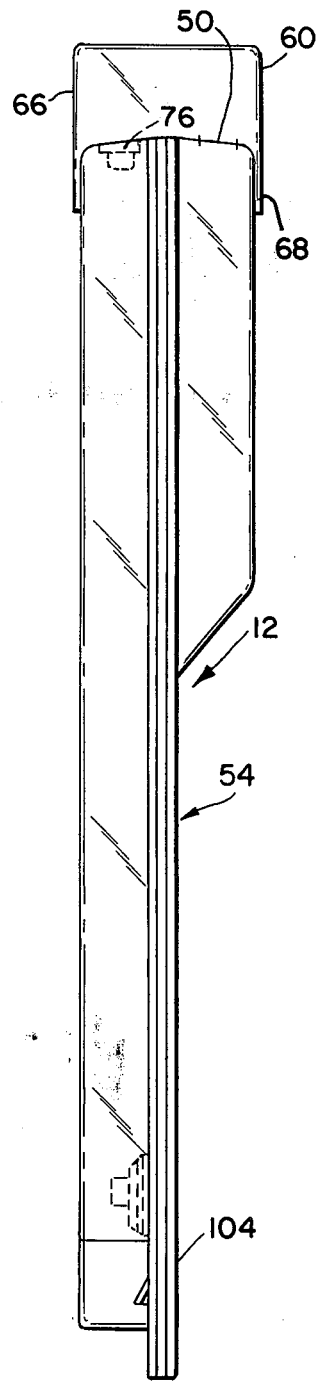
FIG. 2 is an end elevational view taken along line 2—2 in FIG. 1.
Figure 3:
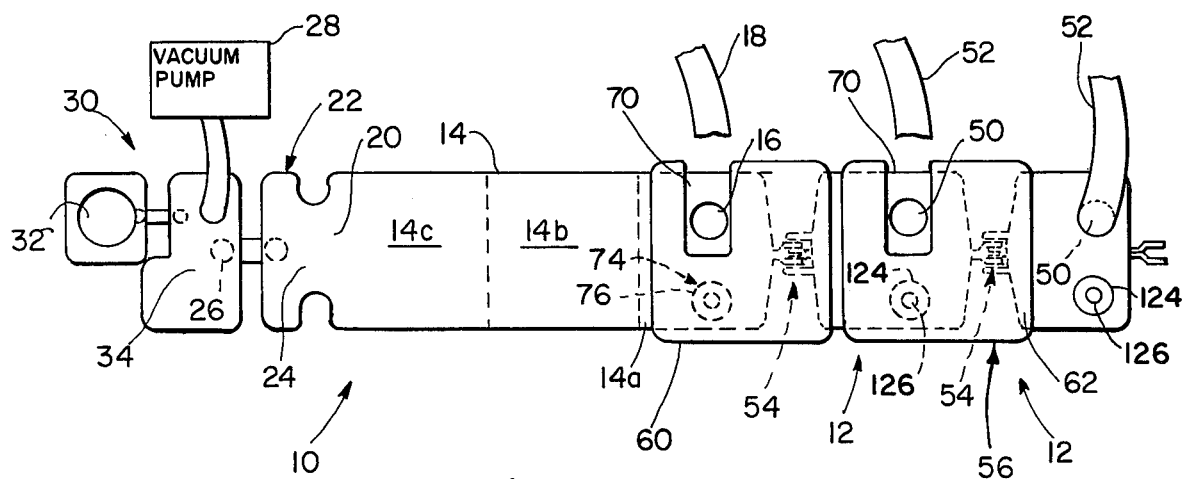
FIG. 3 is a top plan view of one drainage device rigidly connected together to two expansion chambers that are rigidly connected to each other, the three units forming a rigid colinear chain.
Figure 6:
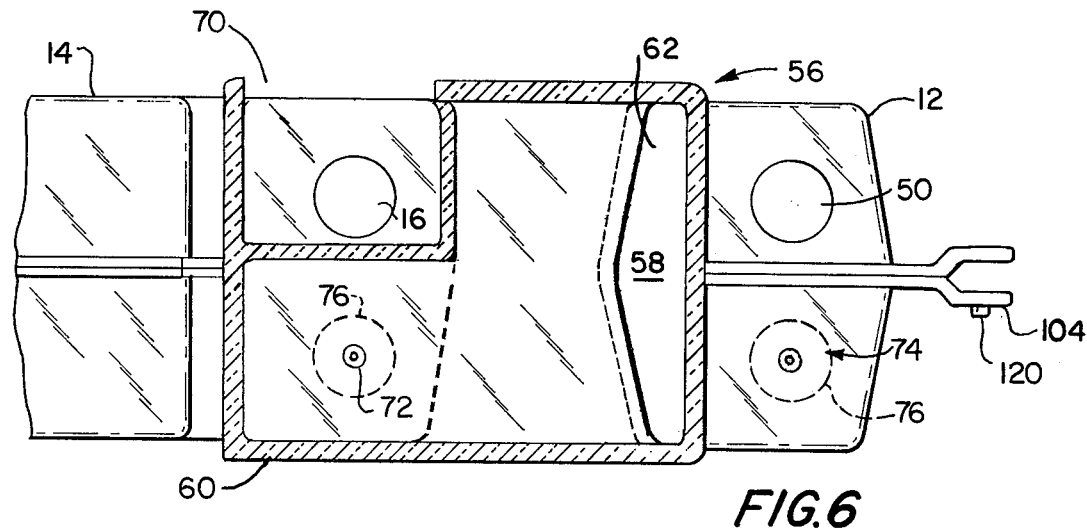
FIG. 6 is a cross sectional view taken along lines 6—6 in FIG. 1, but with parts removed.

Expansion chamber 12 provides an additional collection chamber for the drainage system and, in addition to FIG. 3 referring to FIGS. 1, 2 and 6, comprises an inlet opening 50 adapted to be placed in fluid communication with the cavity to be drained with a thoracotomy tube 52, means for rigidly mounting expansion chamber 12 on drainage device 10 or to another expansion chamber 12 and generally shown at 54, and an equalizing means generally shown at 56 for substantially equalizing the absolute pressure in expansion chamber 12 with the absolute pressure in collection chamber 14 of underwater drainage device 10. An outlet opening 58 in expansion chamber 12 is in communication with a hollow, elongated connecting chamber 60 which in turn is in communication with the top portion of collection chamber 14. Thus, connecting chamber 60 is an equalizing means which places the top or outlet opening 58 of expansion chamber 12 in gaseous communication with a portion of drainage device 10 that is out of contact with the liquid being collected in a collection chamber 14.

One end of connecting chamber 60 is integral with the top of expansion chamber 12 and hence is rigidly mounted thereto. Connecting chamber 60 extends outwardly from the connection to expansion chamber 12 and is substantially coplanar therewith. Connecting chamber 60 is an enclosed passageway that has walls defining a first opening 62 that are generally contiguous with the walls defining outlet 58 of expansion chamber 12 and a second opening 64 at the distal end of connecting chamber 60. Two depending parallel plates 66 and 68 are integral with the side walls of connecting chamber 60. Plates 66 and 68 are transversely spaced apart a distance so as to permit a gripping engagement with the upper part of the side walls of collection chamber 14. A recess 70 in the distal end of connecting chamber 60 permits ready access to collection chamber inlet opening 16.

Rigidly and sealingly secured in connecting chamber second opening 64 is a hollow needle 72 depending from connecting chamber 60. Plates 66 and 68 extend downwardly below needle 72 to provide protection therefor.

Figure 8:
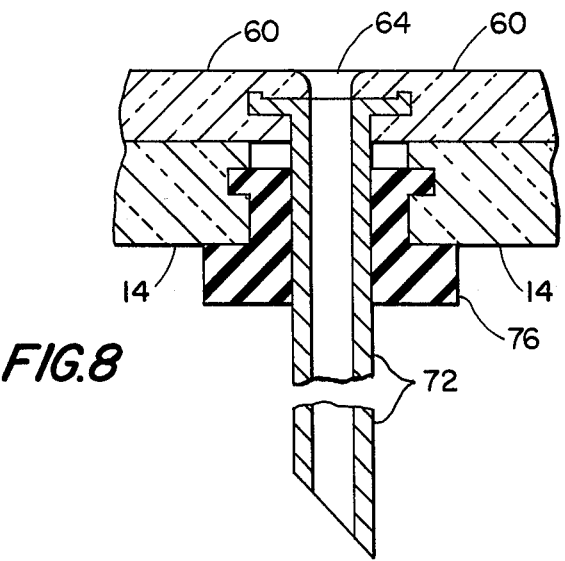
FIG. 8 is an enlarged cross sectional view of the needle of the expansion chamber equalizing means shown in FIG. 7.
Figure 7:
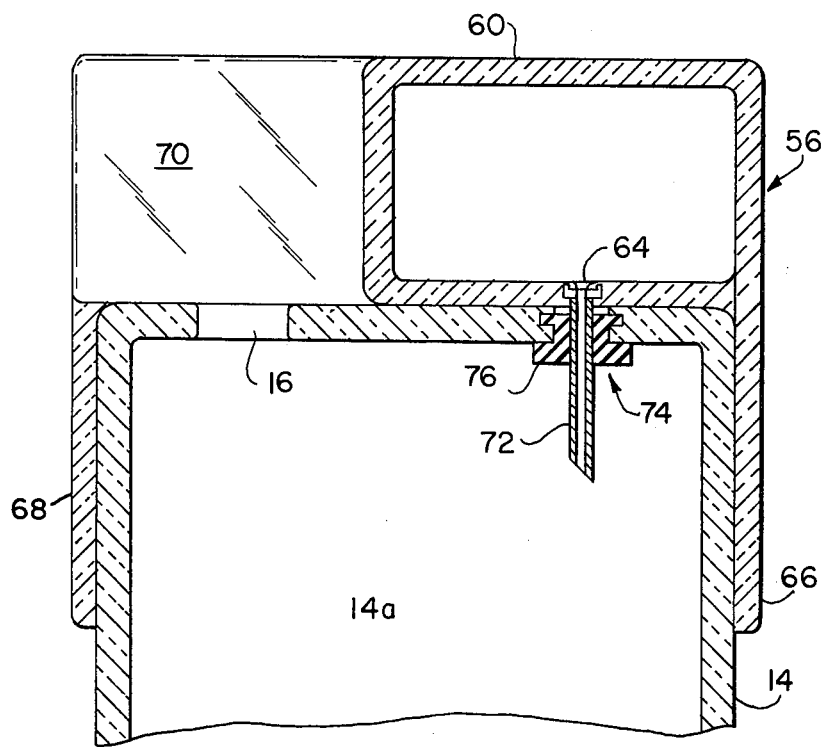
FIG. 7 is a cross sectional view taken along lines 7—7 of FIG. 1 and showing the needle protecting means in engagement with the top of the drainage device.

As best shown in FIGS. 7 and 8, a second or further inlet opening 74 is located in the top portion of collection chamber 14 in transverse alignment with the other inlet opening 16. A resilient, puncturable diaphragm 76 is installed in second opening 74 for completely sealing the opening. Diaphragm 76 can be comprised of a rubber, self sealing grommet. As clearly shown in FIG. 8, diaphragm 76 is rigidly embedded in the top wall of collection chamber 14 with the top wall providing a small diameter opening to permit access to diaphragm 76. Needle 72 is located in connecting chamber 60 such that when expansion chamber 12 is mounted on drainage device 10, needle 72 will be in coaxial alignment with diaphragm 76. Thus, diaphragm 76 provides a normally sealed access that is readily available for being punctured by and receiving therethrough a hollow needle. In this manner, fluid communication can be quickly made between collection chamber 14 and connecting chamber 60.

Figure 4:
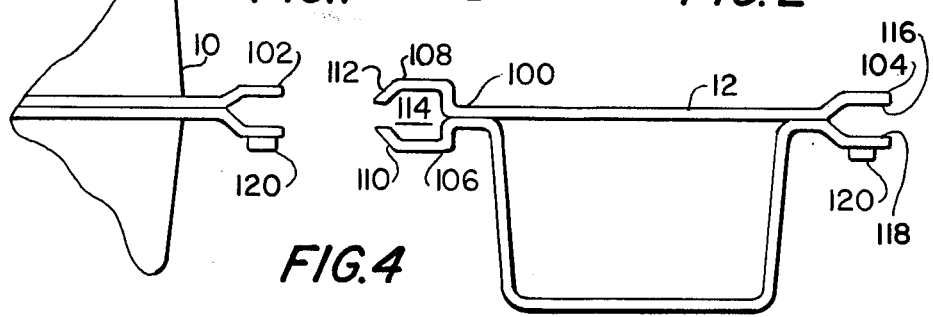
FIG. 4 is an enlarged schematic plan view of a cross section taken essentially along lines 4-4 of FIG. 1, but showing the mounting means uncoupled.

Mounting means 54 are depicted in FIGS. 2, 4, 5, and 6. Mounting means 54 comprises an elongate first rail 100 rigidly mounted along one side thereof and extending substantially coplanar from expansion chamber 12 and an elongated second rail 102 rigidly mounted along one side thereof and extending substantially coplanar from drainage device 10. A third rail 104 is for rigidly mounting to expansion chamber 12 a further, similar expansion chamber (such as shown in FIG. 3). The third rail 104 is rigidly mounted along one side thereof to the other side of expansion chamber 10 opposite the side to which first rail 100 is mounted. Thus, third rail 104 extends substantially coplanar from expansion chamber 12, and hence coplanar with first rail 100, in the opposite direction of first rail 100. As best shown in FIG. 4, first rail 100 comprises in cross section a substantially U-shaped female rail having spaced apart side portions 106 and 108 and terminal end portions 110 and 112 extending toward each other from and respectively rigidly mounted to side portions 106 and 108. Thus, rail 100 has angulated sides which define an interior multi-sided space 114.

Both second rail 102 and third rail 104 are substantially similar and both are male rails for coaxially mating with and being engaged by a female rail such as first rail 100. The outer or exterior cross sectional shape of second and third rails 102 and 104 conform to interior space 114 of first rail 100. Thus, when a male and a female rail are in engagement with each other, the male rail is rigidly secured and attached to the female rail with respect to radial or longitudinal relative movements. In order to provide a snug engagement between the male and female rails, the male rails 102 and 104 are substantially U-shaped in cross section and are comprised of spaced apart sides 116 and 118. Sides 116 and 118 are spaced apart a distance such that they must be compressed to fit inside of interior space 114. Thus, when a male rail is in full engagement with a female rail along the entire length thereof, sides 116 and 118 of the male rail are resiliently urged outwardly and snugly engaged side and terminal end portions 106, 108, 110, and 112. It is noted that the spacing between sides 116 and 118 must be selected so as to also permit relatively easy engagement with the female rail so that an expansion chamber 12 can be rapidly connected to a drainage device 10.

Figure 5:
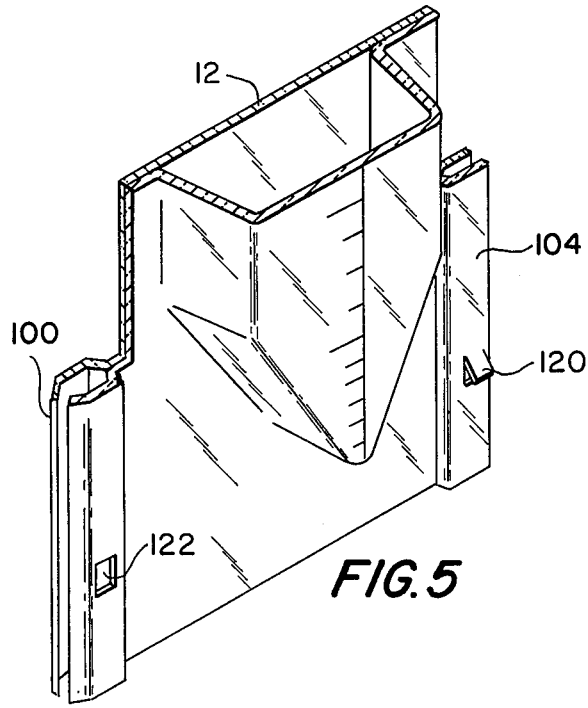
FIG. 5 is a perspective view of a cross section of the expansion chamber showing the mounting means in greater detail.

The configuration of the male and female rails provide secure engagement with respect to longitudinal or radial movements therebetween. In order to prevent axial or vertical movements between the male and female rails, a boss 120 is provided on one of the rails. As shown in FIGS. 4 and 5, boss 120 is comprised of a punched out tab portion located on male rails 102 and 104. A slot 122 in one of the walls of the female rail 100 provides a means for securely receiving boss 120 such that when boss 120 is inserted therein, the male and female rails are substantially locked together with relative coaxial movements therebetween being prevented. Alternatively, boss 120 and slot 122 could be located on the female and the male rails respectively. In addition, boss 120 can be a protrusion on the side of the rail and slot 122 can be a recess in the rail.

In order to permit a chain coupling or "piggy-back" operation of more than one expansion chamber 12 as shown in FIG. 3, expansion chamber 12 is provided with a third opening 124 and a sealing grommet or diaphragm 126 installed therein. The locations and sizes of both expansion chamber inlet opening 50 and third opening 124 with respect to the sides and ends of expansion chamber 12 and with respect to each other, are identical with the locations and sizes of collection chamber inlet opening 16 and second opening 74.

The operation of a pleural drainage device is discussed in detail in the aforementioned Bidwell et al patents. The operation of the present invention is similar to the operation described in these patents. Usually, a underwater drainage device 10 is connected through a thoracotomy tube to a low point in the thoracic cavity. If it is also desired at that time or at a later time to connect a high drain to the thoracic cavity, a second thoracotomy tube, temporarily clamped at one end is connected at the other end to a hight point in the thoracic cavity. It is assumed, for the purposes herein, that underwater drainage device 10 is in operation and is maintaining a vacuum on the thoracic cavity. Thus, neglecting line pressure drops, the vacuum in collection chamber 14 will be substantially the same as the vacuum being maintained inside the thoracic cavity. An expansion chamber 12 according the the present invention is rigidly connected to drainage device 10 by coaxially aligning rails 100 and 102 and sliding rail 100 over and downwardly along rail 102. As rail 100 is being slid downwardly, the lower ends of plates 66 and 68 will engage the sides of drainage device 10 and will place needle 72 into alignment with diaphragm 76. On further downward movement, plates 66 and 68 are forced outwardly by the top of drainage device 10 and needle 72 is inserted into and through diaphragm 76. When rail 100 is securely locked around rail 102 with boss 120 engaging slot 122, the bottom end of needle 72 will have entered collection chamber 14 thereby permitting a vacuum to be established through connecting chamber 60 and into the interior of expansion chamber 12. The second thoracotomy tube, having previously inserted through expansion chamber inlet opening 50, prevents any opening between the interior of expansion chamber 12 and the atmosphere. At this point, the clamp at the end of the second thoracotomy tube can be removed and drainage commenced from the second point in the body cavity.

Similarly, any number of expansion chambers can be quickly connected to the drainage system in a similar manner. Thus a rigid chain of a plurality of collection chambers can be assembled, each collection chamber with its own thoracotomy tube connected to a different point in the body cavity with all of the collection chambers having substantially the same vacuum therein and being regulated by the same vacuum regulator (i.e. manometer 30).

It is noted that a check valve, such as that disclosed in the aforementioned U.S. Pat. 3,809,085, can be inserted into thoracotomy tubes 18 and 52 to permit the development of a high negative pressure in the body cavity for reasons stated in that patent. Although rails 100 and 102 rigidly secure expansion chamber 12 to drainage device 10, it is noted that should the two devices become separated, diaphragm 76 will seal opening 74 and maintain the vacuum inside drainage device 10. If it is desired to provide a means for taking samples from either expansion chamber 12 or drainage device 10, a further opening 128 can be located at the bottom of the respective container and a sealing diaphragm 130 inserted therein. In this manner, a sample of the contents in the respective drainage device or expansion chamber can be taken by using a conventional syringe.

From the above description, it can be seen that an expansion chamber has been provided which permits in inexpensive, rapidly connectable additional collection means to a conventional underwater drainage device whereby the expansion chamber can be independently connected to a separate location in the body cavity being drained, yet, on the other hand can be maintained at the same vacuum as the principal drainage device. Although the invention has been described in detail with respect to an exemplary embodiment thereof, it will be understood by those or ordinary skill in the art that variations and modifications may be effected within the scope and spirit of the invention.

We claim:

1. An expansion chamber directly mountable on a drainage device for draining fluids from a cavity, the drainage device comprising a container having a collection chamber therein, which included an opening in the upper portion thereof and a puncturable diaphragm sealing said opening, and means for placing the collection chamber in fluid communication with the cavity to be drained, wherein the drainage device is adapted to be connected to a source of suction pressure for maintaining a vacuum on the cavity to be drained and is adapted for collecting liquids in the collection chamber thereof, said expansion chamber providing an additional collection chamber and comprising a container having an internal collection chamber;
an inlet opening to said internal collection chamber adapted to be placed in fluid communication with the cavity to be drained;
means for removeably rigidly mounting said expansion chamber on the container of the drainage device such that said expansion chamber and drainage device are integral; and
means for substantially equalizing the absolute pressure in said expansion chamber with the absolute pressure in the collection chamber of the drainage device, said equalizing means including an opening in the upper portion of said expansion chamber and means for placing said expansion chamber upper opening in gaseous communication with a portion of said drainage device out of contact with the liquid being collected therein that comprises means for puncturing said diaphragm and an enclosed passageway sealingly connectable between the interior of said drainage device collection chamber through said diaphragm when punctured and said expansion chamber upper opening.

2. An expansion chamber as claimed in claim 1 wherein the said drainage device upper opening is located in the top portion of the said drainage collection chamber, said puncturable diaphragm being resilient, and wherein said puncturing means includes a hollow needle for puncturing the diaphragm and said passageway connects said hollow needle with the expansion chamber opening.

3. An expansion chamber directly mountable on a drainage device for draining fluids from a cavity, the drainage device comprising a container having a collection chamber therein and means for placing the collection chamber in fluid communication with the cavity to be drained, said expansion chamber providing an additional collection chamber and comprising a container having an internal collection chamber;
an inlet opening to said internal collection chamber adapted to be placed in fluid communication with the cavity to be drained;
means for removeably rigidly mounting said expansion chamber on the container of the drainage device such that said expansion chamber and drainage device are integral;
means for substantially equalizing the absolute pressure in said expansion chamber with the absolute pressure in the collection chamber of the drainage device; and
wherein said equalizing means comprises an opening in the top of said expansion chamber, a hollow, elongate connecting chamber rigidly mounted at one end thereof to the top of said expansion chamber and in fluid communication with said top opening, and means for placing said connecting chamber in fluid communication with said drainage device.

4. An expansion chamber as claimed in claim 3 wherein said communication placing means comprises a hollow needle depending from and in communication with the other end of said connecting chamber.

5. An expansion chamber as claimed in claim 4 wherein said connecting chamber extends outwardly from said one end beyond said expansion chamber and substantially coplanar therewith and wherein said connecting chamber further comprises means for protecting said needle.

6. An expansion chamber as claimed in claim 5 wherein the drainage device includes side walls; said connecting chamber includes said walls; and said protecting means comprises two parallel plates depending from and rigidly mounted to said side walls of said connecting chamber at said other end thereof; said plates each extending below said needle and transversely spaced apart a sufficient distance so as to grippingly engage the side walls of the drainage device.

7. An expansion chamber as claimed in claim 3 and further comprising means for rigidly mounting thereto a further similar expansion chamber.

8. An expansion chamber as claimed in claim 7 wherein said communication placing means comprises a hollow needle depending from and in communication with the other end of said connecting chamber; and further includes a second opening in the top of said expansion chamber and a resilient, puncturable diaphragm sealing said second top opening for being punctured by the hollow needle of said further expansion chamber.

9. An expansion chamber directly mountable on a drainage device for draining fluids from a cavity, the drainage device comprising a container having a collection chamber therein and means for placing the collection chamber in fluid communication with the cavity to be drained, said expansion chamber providing an additional collection chamber and comprising
a container having an internal collection chamber;
an inlet opening to said internal collection chamber adapted to be placed in fluid communication with the cavity to be drained;
means for removeably rigidly mounting said expansion chamber on the container of the drainage device such that said expansion chamber and drainage device are integral;
means for substantially equalizing the absolute pressure in said expansion chamber with the absolute pressure in the collection chamber of the drainge device; and
wherein said mounting means comprises an elongated first rail rigidly mounted along one said thereof and extending substantially coplanar from said expansion chamber and an elongated second rail slidably engagable with said first rail and rigidly mounted along one side thereof and extending substantially coplanar from the drainage device.

10. An expansion chamber as claimed in claim 9 wherein one of said first and second rails comprises in cross section a substantially U-shaped female rail having spaced apart side portions and terminal end portions extending toward one another from and rigidly mounted to the corresponding side portion; and wherein the other one of said first and second rails comprises a male rail for coaxially mating with and being engaged by said female rail, said male rail having an outer cross sectional shape conforming to the inner cross sectional shape of said female rail such that when in engagement therewith, said male rail is rigidly secured and attached to said female rail with respect to relative longitudinal movement.

11. An expansion chamber as claimed in claim 10 wherein one of said male and female rails comprises in cross section a transversely extending boss and the other one of said male and female rails comprises in cross section, a means for securely receiving said boss such that when said boss is received thereby, said male and female rails are substantially locked together thereby preventing relative coaxial movement therebetween.

12. An expansion chamber as claimed in claim 11 wherein said expansion chamber further comprises further means for rigidly mounting to said expansion chamber a further similar expansion chamber, said further mounting means comprising said second elongate rail rigidly mounted along one side thereof to said expansion chamber extending substantially coplanar therefrom in the opposite direction of said first rail.

13. In a drainage device for draining extraneous fluid from a cavity and for applying a vacuum to the cavity comprising a collection chamber and an underwater seal chamber, said collection chamber having located at its upper end an inlet and an outlet opening, the inlet opening adapted to be placed in fluid communication with the cavity to be drained, said seal chamber also having located at its upper end an inlet opening and an outlet opening, the seal chamber inlet opening being in fluid communication with the collection chamber outlet opening and exposed to pressure conditions in the collection chamber, the seal chamber outlet opening being exposed to pressure conditions other than the pressure conditions in the collection chamber, the improvement wherein said drainage device further includes an expansion chamber mounted thereon for also draining fluids from the aforesaid cavity, the expansion chamber comprising means for rigidly mounting said expansion chamber on said drainage device; an inlet opening in said expansion chamber adapted to be placed in fluid communication with the aforesaid cavity; an outlet opening in said expansion chamber; and means for exposing said expansion chamber outlet opening to pressure conditions in the collection chamber.

14. A drainage device as claimed in claim 13 wherein the drainage device further includes an opening in a top portion of a part of the drainage device that when in operation normally has a vacuum therein, and a resilient, puncturable diaphragm sealing the top opening in the drainage device, and wherein said pressure exposing means includes a hollow needle for puncturing the diaphragm and a passageway connecting said hollow needle with said outlet opening of said expansion chamber.

15. A drainage device as claimed in claim 13 wherein said expansion chamber further comprises an outlet top opening located in the top of said expansion chamber, and said exposing means comprises a hollow, elongate connecting chamber rigidly mounted at one end thereof to the top of said expansion chamber and in fluid communication with said outlet top opening, and said exposing means places said connecting chamber in fluid communication with said drainage device.

16. A drainage device as claimed in claim 15 wherein said exposing means further comprises a hollow needle depending from and in communication with the other end of said connecting chamber.

17. A drain device as claimed in claim 16 wherein said connecting chamber extends outwardly from said one end beyond said expansion chamber and substantially coplanar therewith and wherein said connecting chamber further comprises means for protecting said needle.

18. A drainage device as claimed in claim 17 wherein the drainage device includes side walls; said connecting chamber further includes side walls; and said protecting means comprises two parallel plates depending from and rigidly mounted to said side walls of said connecting chamber at said other end thereof; said plates each extending below said needle and transversely spaced apart a sufficient distance so as to grippingly engage the side walls of the drainage device.

19. A drainage device as claimed in claim 15 and further comprising means for rigidly mounting thereto a further similar expansion chamber.

20. A drainage device as claimed in claim 19 wherein said communication placing means comprises a hollow needle depending from and in communication with the other end of said connecting chamber; and further includes a second opening in the top of said expansion chamber and a resilient, puncturable diaphragm sealing said second top opening for being punctured by the hollow needle of said further expansion chamber.

21. A drainage device as claimed in claim 13 wherein said mounting means comprises an elongated first rail rigidly mounted along one side thereof and extending substantially coplanar from said expansion chamber and an elongated second rail slidably engageable with said first rail and rigidly mounted along one side thereof and extending substantially coplanar from the drainage device.

22. A drainage device as claimed in claim 21 wherein one of said first and second rails comprises in cross section a substantially U-shaped female rail having spaced apart side portions and terminal end portions extending toward one another from and rigidly mounted to the corresponding side portion; and wherein the other one of said first and second rails comprises a male rail for coaxially mating with and being engaged by said female rail, said male rail having an outer cross sectional shape conforming to the inner cross sectional shape of said female rail such that when in engagement therewith, said male rail is rigidly secured and attached to said female rail with respect to relative longitudinal movement.

23. A drainage device as claimed in claim 22 wherein one of said male and female rails comprises in cross section, a transversely extending boss and the other one of said male and female rails comprises, in cross section, a means for securely receiving said boss such that when said boss is received thereby, said male and female rails are substantially locked together thereby preventing relative coaxial movement therebetween.

24. A drainage device as claimed in claim 23 wherein said expansion chamber further comprises further means for rigidly mounting to said expansion chamber a further similar expansion chamber, said further mounting means comprising said second elongate rail rigidly mounted along one side thereof to said expansion chamber extending substantially coplanar therefrom in the opposite direction of said first rail.

25. In combination with a drainage device for draining extraneous fluid from a cavity and for applying a vacuum to the cavity comprising a collection chamber and an underwater seal chamber, said collection chamber having located at its upper end an inlet and an outlet opening, the inlet opening adapted to be placed in fluid communication with the cavity to be drained, said seal chamber also having located at its upper end an inlet opening and an outlet opening, the seal chamber inlet opening being in fluid communication with the collection chamber outlet opening and exposed to pressure conditions in the collection chamber, the seal chamber outlet opening being exposed to pressure conditions other than the pressure conditions in the collection chamber, an expansion chamber mountable on said drainage device for also draining fluids from the aforesaid cavity, the expansion chamber comprising means for rigidly mounting said expansion chamber on said drainage device; an inlet opening in said expansion chamber adapted to be placed in fluid communication with the aforesaid cavity; an outlet opening in said expansion chamber; and means for exposing said expansion chamber outlet opening to pressure conditions in the collection chamber.

26. A drainage device combination as claimed in claim 26 wherein the drainage device further includes an opening in a top portion of a part of the drainage device that when in operation normally has a vacuum therein, and a resilient, puncturable diaphragm sealing the top opening in the drainage device; and wherein said pressure exposing means includes a hollow needle for puncturing the diaphragm and a passageway connecting said hollow needle with said outlet opening of said expansion chamber, said outlet opening of said expansion chamber being located in the top thereof.

* * * * *